(12) United States Patent
Benson (10) Patent No.: US 10,234,452 B2
(45) Date of Patent: Mar. 19, 2019

(54) ASSAY DEVICE

(75) Inventor: Jennifer Mary Benson, Milton Keynes (GB)

(73) Assignee: WORLDWIDE PRODUCT SOURCING LIMITED, Middlesex (GB)

(*) Notice: Subject to any disclaimer, the term of this patent is extended or adjusted under 35 U.S.C. 154(b) by 0 days.

(21) Appl. No.: 13/390,154

(22) PCT Filed: Aug. 10, 2010

(86) PCT No.: PCT/GB2010/001513
§ 371 (c)(1),
(2), (4) Date: Mar. 1, 2012

(87) PCT Pub. No.: WO2011/018618
PCT Pub. Date: Feb. 17, 2011

(65) Prior Publication Data
US 2012/0148458 A1    Jun. 14, 2012

(30) Foreign Application Priority Data
Aug. 11, 2009 (GB) .................................. 0914001.3

(51) Int. Cl.
*G01N 33/50* (2006.01)
*G01N 33/543* (2006.01)
*B01L 3/00* (2006.01)

(52) U.S. Cl.
CPC ...... *G01N 33/54386* (2013.01); *B01L 3/5023* (2013.01); *B01L 2300/0825* (2013.01); *B01L 2300/12* (2013.01); *B01L 2400/0406* (2013.01)

(58) Field of Classification Search
USPC ........................................................ 422/401
See application file for complete search history.

(56) References Cited

U.S. PATENT DOCUMENTS 5,155,155 A * 10/1992 Jurlaro ........................... 524/275
5,565,503 A * 10/1996 Garcia et al. ................. 523/124
(Continued)

FOREIGN PATENT DOCUMENTS

WO       2008006492 A1     1/2008

OTHER PUBLICATIONS

International Search Report for PCT/GB2010/001513 dated Mar. 4, 2011.
(Continued)

*Primary Examiner* — Jill A Warden
(74) *Attorney, Agent, or Firm* — Heslin Rothenberg Farley & Mesiti P.C.

(57) ABSTRACT

An assay test device, suitable for use as a home pregnancy test kit, comprises a casing and two test panels mounted to an elongate arm. The test panels are held within the casing for storage. Manual operation of a slider causes the test panels to project outwardly from an end of the casing, so that a liquid test sample may be administered to the panels. The panels are then withdrawn into the casing, which has a window allowing the test panels to be observed while the test reaction (typically an ELISA test) takes place. Indicia may be applied to reveal messages when a test panel changes color. The casing and other components comprise a polyolefin treated to be oxo-biodegradable or biodegradable, so that they may rapidly break down in aerobic conditions on disposal.

19 Claims, 7 Drawing Sheets

(56) References Cited

U.S. PATENT DOCUMENTS

| | | | | |
|---|---|---|---|---|
| 7,090,802 | B1* | 8/2006 | Wang | B01L 3/5023 |
| | | | | 422/417 |
| 2002/0192715 | A1* | 12/2002 | Degelaen et al. | 435/7.1 |
| 2006/0133956 | A1* | 6/2006 | Hamanaka | 422/68.1 |
| 2006/0199277 | A1* | 9/2006 | Tang | G01N 33/558 |
| | | | | 436/514 |
| 2008/0087865 | A1* | 4/2008 | Ferdinand et al. | 252/404 |
| 2008/0103232 | A1* | 5/2008 | Lake et al. | 523/124 |
| 2008/0286879 | A1* | 11/2008 | Lee | 436/164 |

OTHER PUBLICATIONS

Reddy M M et al; "Biodegradation of oxo-biodegradable polyethylene," Journal of Applied Polymer Science, Feb. 5, 2009, pp. 1426-1432, vol. 111, No. 3.

Vogt N B et al; "Oxo-biodegradable polyolefins show continued and increased thermal oxidative degradation after exposure to light," Polymer Degradation and Stability, Apr. 2009, pp. 659-663, vol. 94, No. 4.

* cited by examiner

ASSAY DEVICE

CROSS REFERENCE TO RELATED APPLICATIONS

This application is a national stage filing under section 371 of International Application No. PCT/GB2010/001513 filed on Aug. 10, 2010, and published in English on Feb. 17, 2011 as WO 2011/018618 A2 and claims priority of Great Britain application No. 0914001.3 filed on Aug. 11, 2009, the entire disclosure of these applications being hereby incorporated herein by reference.

BACKGROUND ART

The present invention relates to devices for performing chemical and biochemical assays, particularly for medical/health purposes. More particularly but not exclusively, it relates to devices for performing pregnancy tests, especially such devices for non-professional use.

It is well known for women to determine if they are pregnant using specialist test devices intended for personal use without the assistance of medical professionals (such devices are generally known as home pregnancy test kits). These devices are usually based on a biochemical immunoassay, testing for the presence of elevated levels of the hormone human chorionic gonadotrophin (hCG) in body fluids, such as urine. The hCG hormone is generated from the very early stages of pregnancy, and so is a very useful indicator species. The immunoassay is generally based on the use of antibodies to hCG and of antigens adapted to couple with such antibodies, at binding sites on the antibody known as epitopes.

The pregnancy test devices first made available relied on urine permeating along a test strip of paper or similar material. A reservoir of hCG antibodies bound to a coloured particulate material (such as colloidal gold or pigmented latex) is encountered first. If hCG is present, the antibodies couple thereto, forming a complex which is carried along the test strip. Further along the test strip is a transverse linear zone of an anchored reagent to which the hCG/antibody complex will bind. Thus, if hCG is present in the urine, the hCG/antibody complex and the associated coloured material will accumulate in this zone, forming a visible coloured line across the test strip.

This approach is widely used, but has led to some problems in practice. In the very early stages of pregnancy, hCG levels are relatively low, and the coloured line may well be faint. This can lead to both false positive and false negative results (reviews have indicated better than 97% accuracy when used by experienced technicians, but as low as 75% when used by the general public). Some users apparently have difficulty in interpreting the presence of a line, even when hCG levels are high.

An alternative approach has thus been to measure the hCG/antibody levels electronically (e.g. by colorimetry), and to use the measured levels to trigger verbal messages on a display screen, such as "Pregnant" or Not Pregnant". These devices remove much of the human error from the procedure, but are more expensive, due to the need to provide a sensor system, a control chip, a display screen (e.g. an LCD display) and a power source. Additionally, these components are not practical or economic to recycle, but will not break down in landfill or other waste disposal routes.

It would therefore be beneficial if test devices could be produced that gave similarly definite results but without requiring expensive and environmentally unfriendly components.

Tens of millions of home pregnancy test kits of all types are produced, used and discarded every year. There are hence significant waste disposal problems with all current forms of pregnancy testing device, even the non-electronic types.

A further issue is hygiene. At present, it is necessary to dip an end of the test device into a retained urine sample, or more usually the user urinates directly on to the end of the test device. In each case the use should then replace a plastics cap over the urine soaked end of the test device. These caps are a snug fit to obviate leakage, but if the user is not completely accurate in replacing the cap, and inadvertently touches the urine-soaked end of the test strip, or if the user places the used test device on an unsterilised surface before replacing the cap, cross-contamination may occur, which may effect the result of the test. This is also a problem requiring attention.

While the above discussion is expressed in terms of pregnancy tests, there is now a wide range of further, similar assay tests for a variety of medical conditions, working on the immunoassay principle to test urine, blood or other body fluids. In each case, the above problems with accurate and clear display of the results, and with disposal of used test devices, will also apply.

For immunoassay tests for serious conditions such as HIV/AIDS, overspill of test fluids could be particularly undesirable and hazardous. Nevertheless, test devices for such conditions will be required to be usable in non-laboratory, non-ideal conditions, particularly in the developing world.

It is hence an object of the present invention to provide an immunoassay testing device, particularly a pregnancy testing device, that obviates some or all of the above drawbacks of existing devices.

BRIEF SUMMARY OF INVENTION

According to a first aspect of the present invention, there is provided an immunoassay testing device comprising immunoassay testing means mounted to structure means, said structure means comprising casing means adapted to enclose the immunoassay testing means, wherein the casing means comprises a plastics material adapted to be environmentally degradable.

Preferably, substantially all of the structure means of the device comprises said environmentally degradable plastics material.

In a preferred embodiment, the plastics material comprises an oxo-biodegradable plastics material, so adapted that its degradation is initiated by reaction with oxygen.

The oxo-biodegradable plastics material may be so adapted that its degradation is initiated by reaction with both oxygen and water.

Advantageously, the oxo-biodegradable plastics material is adapted to complete its environmental degradation under microbiological action.

Optionally, the oxo-biodegradable plastics material is also adapted to complete its environmental degradation without microbiological action, for example by aerial oxidation alone.

Alternatively, the environmentally degradable plastics material may comprise a plastics material filled with particles of a more readily biodegradable material.

Said readily biodegradable material may comprise a naturally-occurring polymeric material, such as starch.

Preferably, the environmentally degradable plastics material comprises a polyolefin polymer.

Said polyolefin polymer may comprise polyethylene and/or polypropylene.

The environmentally degradable plastics material preferably comprises a plastics material blended with an additive adapted to promote oxidative degradation of the plastics material.

Said oxidative degradation may comprise oxidative cleavage of long-chain polymer molecules within the plastics material.

The cleavage of said long-chain polymer molecules may thus produce chain fragments sufficiently short to be attacked and degraded further by microorganisms.

Oxidative cleavage of said long-chain polymer molecules may also generate polar chemical groups on the molecules or fragments thereof, increasing wettability of the plastics material by water and/or promoting biofilm growth on the plastics material.

Preferably, said additive to promote oxidative degradation comprises at least one metal salt.

Advantageously, said additive to promote oxidative degradation comprises a hydrocarbon material, such as naphtha.

Said immunoassay test device may comprise a pregnancy test device.

According to a second aspect of the present invention, there is provided an immunoassay testing device comprising immunoassay test means and casing means, wherein the test means is selectably displaceable between a first disposition extending outwardly from the casing means and a second disposition substantially enclosed within the casing means.

Preferably, the test means is slideable between said two dispositions.

Advantageously, the test means is adapted to receive a sample for testing in the first disposition and for the immunoassay test to be carried out in the second disposition.

The test means may comprise an elongate body displaceable generally along its longitudinal axis.

The test means may be manually displaceable between said two dispositions.

Optionally, the device is provided with manual displacement means, remote from but directly or indirectly operably connected to the test means.

The casing means is preferably provided with window means permitting observation of the test means in said second disposition.

The immunoassay testing device may comprise a pregnancy testing device.

According to a third aspect of the present invention, there is provided an immunoassay test device comprising immunoassay test means, wherein said test means is adapted to produce, as an indication of a positive test result, a colour change extending across a two-dimensional zone of test material.

Preferably, the test device comprises casing means provided with window means permitting observation of said two-dimensional zone.

In a preferred embodiment, said two-dimensional zone comprises regions so treated as not to undergo said colour change in the event of a positive result.

Said treatment may comprise printing on said regions with a water-repellant composition.

Said treatment may comprise omission from said regions of a material necessary for said colour change, or printing thereon with a reagent to inactivate said material.

Said treatment may comprise printing on said regions with an agent that contrasts with a remainder of the two dimensional zone following a positive test result.

Said regions may form indicia, such that the indicia will become visible due to the colour change in a remainder of the zone outside said regions.

Said colour change may be due to a coloured species migrating from outside the zone becoming immobilised in said zone.

Said colour change may be due to a colour-producing reaction between a first species migrating from outside the zone and a second species present in the zone.

The device may be provided with a plurality of said zones of test material.

The immunoassay test device may comprise a pregnancy test device.

According to a fourth aspect of the present invention, there is provided an immunoassay test device comprising a composition containing magnetic particles and adapted to be released from a substrate by the presence of a preselected biomolecule, and a zone of magnetic material remote from said substrate, said zone being adapted to capture magnetically said released composition migrating through the zone.

Preferably, said composition comprises a coloured material, such that capture thereof by the zone of magnetic material is visibly distinguishable.

Optionally, the coloured material may comprise said magnetic particles.

Alternatively, said composition may comprise a first species adapted to react with a second species located in said zone to produce a coloured material.

The zone of magnetic material may comprise a substantially one-dimensional line.

Alternatively, the zone of magnetic material may comprise a two-dimensional zone.

The zone of magnetic material may be adapted to form indicia.

The immunoassay test device may comprise a pregnancy test device.

According to a fifth aspect of the present invention, there is provided an immunoassay test device having a combination of features from any two or more of the first to fourth aspects above.

BRIEF DESCRIPTION OF DRAWING FIGURES

Embodiments of the present invention will now be more particularly described by way of example and with reference to the accompanying drawings in which.

DETAILED DESCRIPTION

Figure 1:
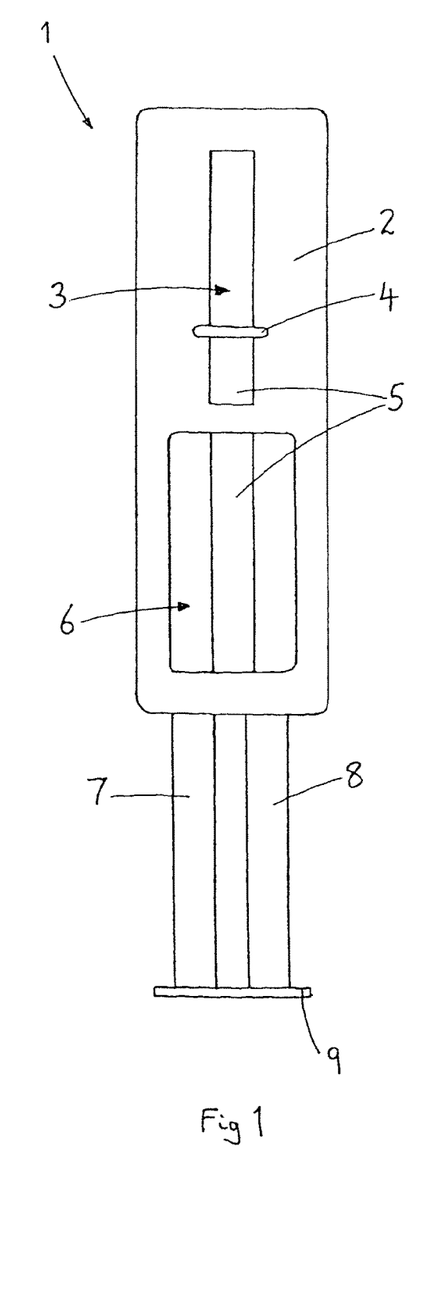
FIG. 1 is a frontal elevation of a first assay device embodying the present invention, with its test panels extended.
Figure 2:
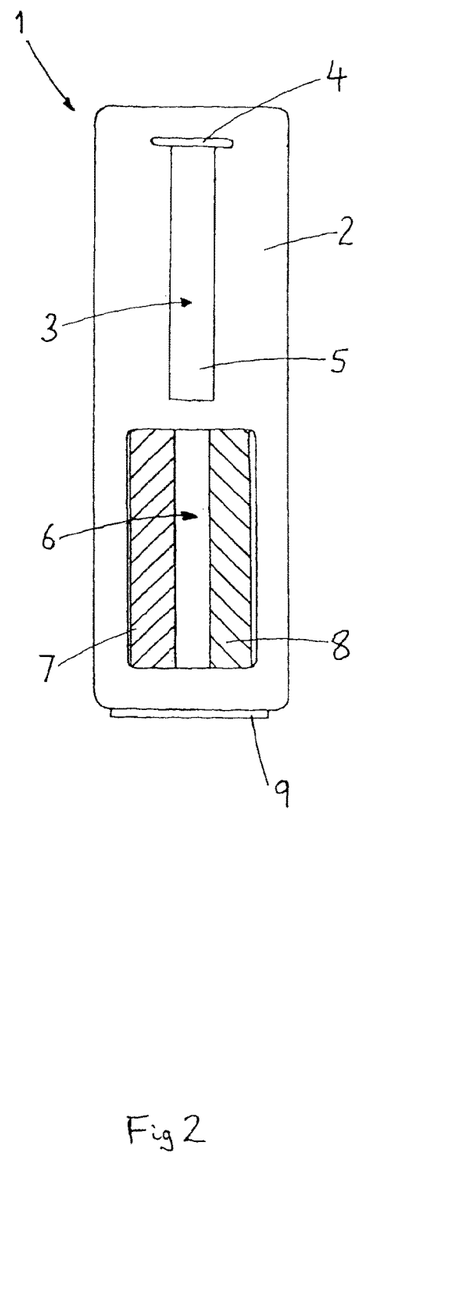
FIG. 2 is a frontal elevation of the assay device shown in FIG. 1, with its test panels refracted.

Referring now to the Figures, and to FIGS. 1 and 2 in particular, an assay device 1 embodying the present invention is shown. The invention will be described below mainly in terms of its embodiments comprising home pregnancy test kits, but the assay device 1 shown is equally suitable for a range of other chemical and (particularly) biochemical assays and tests.

Figure 5:
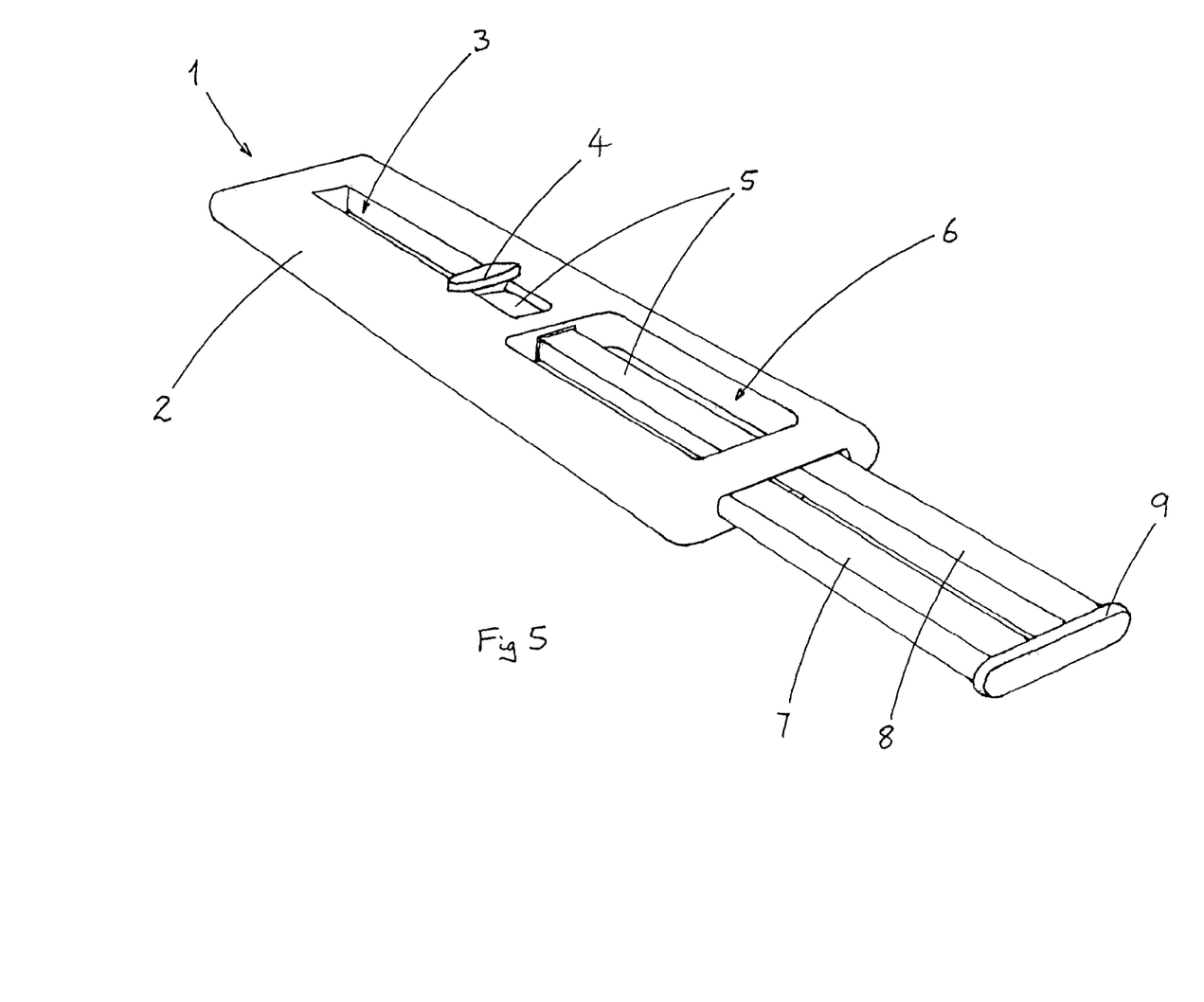
FIG. 5 is a perspective view of the assay device shown in FIG. 1, with its test panels extended.

The assay device 1 comprises a casing 2 having an elongate, slim rectangular shape (see also FIG. 5 for an overall view of its shape). A longitudinal slot 3 runs along a front face of the assay device 1, from adjacent a first end of the casing 2 to adjacent a midpoint thereof. A manually-operable slider 4 is constrained to travel along the slot 3. The slider 4 is mounted to a first end of an elongate piston arm 5, which is thus also movable longitudinally.

A rectangular window 6 is formed in the front face of the casing 2, disposed between the slot 3 and a second end of the casing 2 remote from the first. The window 6 may comprise a simple aperture in the casing 2, or may be covered by a clear vision panel. Optionally, this clear panel may be profiled to magnify a user's view of an interior of the casing 2 behind the window 6.

In this particular embodiment, an elongate first test panel 7 and an elongate second test panel 8 are each mounted at a proximal end to a second end of the piston arm 5 remote from the slider 4, each test panel 7, 8 extending side-by-side longitudinally of the device 1. Each test panel 7, 8 comprises a thin, porous substrate (typically a form of paper) supported on a rigid backing plate. A transverse end cap 9 connects a distal end of each test panel 7, 8 (NB for some assays, a single test panel may be sufficient).

Figure 3:
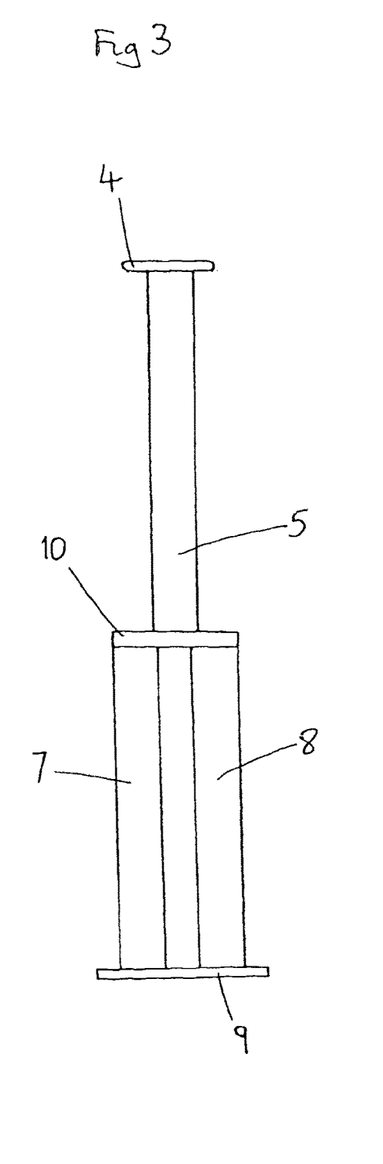
FIG. 3 is a frontal elevation of a test panel assembly separated from the assay device shown in FIG. 1.

As shown in FIG. 3, a cross-bar 10 (obscured in FIGS. 1 and 2) connects the proximal ends of the test panels 7, 8 to the piston arm 5. The entire assembly shown in FIG. 3 may thus be moved longitudinally as a unit by manual movement of the slider 4.

Figure 4:
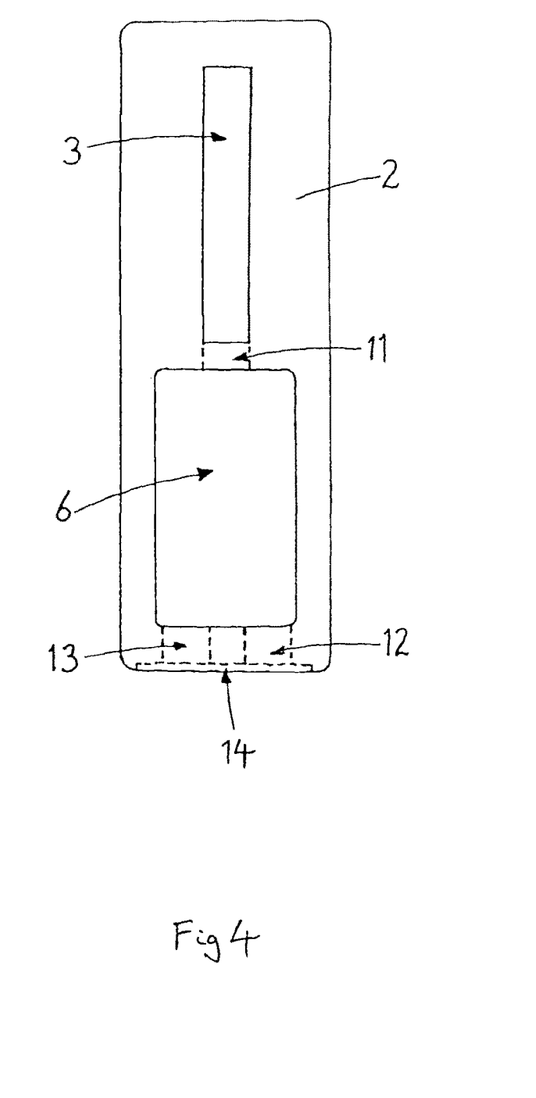
FIG. 4 is a frontal elevation of a casing of the assay device shown in FIG. 1.

FIG. 4 shows the casing 2 in more detail. In most embodiments, the casing 2 comprises two cooperable mouldings, which are assembled to form a hollow shell. If desired, a partially solid body may be provided in place of such a hollow moulding. The casing 2, the slider 4, the piston arm 5, the backing to the test panels 7, 8 and most other parts of the assay device 1 are in most cases moulded from plastics material, ideally a polyolefin such as polyethylene or polypropylene. This plastics material is preferably modified to be biodegradable, as described in more detail below.

The casing 2 may comprise an internal passage 11 linking the slot 3 and the window 6, the passage 11 being configured to receive and guide the piston arm 5. Alternatively, guide rails, pairs of rollers, pairs of guide posts or other such features may be provided within the casing 2, to ensure that the piston arm 5 (and everything attached thereto) travels essentially longitudinally.

At the second end of the casing 2, a pair of apertures 12, 13 extend through the casing 2, being configured to receive and guide a respective test panel 7, 8. Alternatively, a single aperture may be provided, through which both test panels 7, 8 pass. A recess 14 may be provided in the casing 2 to receive the end cap 9.

In an alternative arrangement (not shown), the piston arm 5 extends outwards from the first end of the casing 2 and terminates in a push-button, thus forming a structure resembling a syringe plunger. This assay device otherwise resembles that shown in FIGS. 1 to 4, apart from not requiring a slot 3 to contain a slider 4.

The assay device 1 thus has two selectable configurations, as shown in FIGS. 1 and 2 respectively. It is stored in the configuration of FIG. 2, with the slider 4 at the first end of the slot 3, the piston arm 5 held within the slot 3, and the test panels 7, 8 held within the casing 2, behind the window 6. The second end of the casing is closed by the end cap 9 (which ideally sits sealingly in the recess 14).

For use, the slider 4 is moved down the slot 3, the piston arm 5 travelling into the portion of the casing 2 behind the window 6, and the test panels 7, 8 projecting longitudinally from the casing 2, as shown in FIG. 1. In this configuration, a liquid test sample (e.g. a user's urine for a pregnancy test) may be poured or projected over the test panels 7, 8, or the test panels 7, 8 may be dipped into a reservoir of a liquid test sample.

Once the test sample has thus been administered to the test panels 7, 8, the slider 4 is returned to the first end of the slot 3, withdrawing the test panels 7, 8 into the casing 2 (i.e. returning to the configuration of FIG. 2). The relevant test reactions on the test panels 7, 8 (see below) may be observed through the window 6.

A major benefit of this arrangement is hygiene. Conventional assay devices, such as home pregnancy test kits, usually involve a user urinating on a permanently exposed end portion of a test panel, or dipping this test panel into urine. It is very easy to misdirect the urine over the casing of a conventional device, leading to subsequent contamination of the user's fingers and/or the surrounding area while the test is being followed. There are even greater potential hazards when other bodily fluids, such as blood, are being tested, particularly when the test is for an infectious disease.

The test panels 7, 8 extending from the assay device 1 of the present invention make it much easier to apply a liquid test sample to the test panels 7, 8 alone. When the test panels 7, 8 are retracted within the casing 2, a potentially hazardous test sample applied to the panels 7, 8 is safely held within the casing 2 (especially when the window 6 is glazed and the end cap 9 sits sealingly in a recess 14). The worst case scenario with such an arrangement would be for there to be a tiny amount of contamination on the outside of the end cap 9, and this, too, could be obviated by a deeper recess 14 within which to withdraw the end cap 9 completely.

The actual test reaction can be selected from a range of known test systems, depending on the analyte to be assayed. One commonly-used class of test systems is generally referred to as "lateral flow tests". A liquid test sample flows through a porous substrate, usually by capillary action. It first encounters a reservoir of a coloured material, which becomes entrained into the flowing liquid sample. The coloured material (typically a particulate material, such as colloidal gold or a pigmented latex) is usually pre-treated so that the particular analyte binds to the coloured material. For example, specific antibodies to the analyte may be bonded to the coloured material, so that the analyte in turn becomes attached via the antibodies to the coloured material. In the absence of the particular analyte, the coloured material is simply entrained with the test sample.

The test sample then enters a detection zone, in which there is an anchored reagent that also binds to the analyte. The analyte and the coloured material attached thereto are thus immobilised in this detection zone, where the accumulation of coloured material produces a visual indication of the presence of the analyte in the test sample. If the analyte is not present, the coloured material is not captured by the anchored reagent, and continues in suspension in the test sample, out of the detection zone.

This arrangement is conventionally used is pregnancy tests, as described in the introductory section above. The analyte assayed is then hCG (human chorionic gonadotrophin).

However, this is not the only arrangement by which analyte/antibody reactions may be used to produce a visual display of the presence of the analyte. The general term for such systems relying on analyte/antibody reactions in ELISA, or "enzyme-linked immunosorbent assay". A wide range of ELISA systems are available. For example, in some systems, the coloured material might only be released from the substrate if the analyte is present. Thus, the coloured material only passes onwards in the test sample to the detection zone, if the analyte is present. The detection zone may then contain an anchored reagent adapted to immobilise the coloured material directly, instead of one adapted to immobilise the analyte.

Another approach is to employ a two-component colour indicator system, with a colourless dye precursor being entrained in the test sample in the reservoir zone when the analyte is present. The detection zone is then provided with a reagent that reacts with the dye precursor to form a coloured product. Alternatively, the precursor may be a different colour to the dye or pigment generated in the detector zone, and/or the dye/pigment generated may be a more intense shade than the precursor. In each case, an interaction between the analyte and an antibody for the analyte is used to release the dye precursor, to capture the dye precursor in the detection zone, or both.

It will be noted that the assay device 1 described above has two test panels 7, 8. A frequent issue with such tests relying on a colour change in a detection zone is that low levels of analyte (e.g. low levels of hCG in the early stages of pregnancy) may lead to unclear results. Thus, it may well be beneficial to provide a comparator to show what a positive result should look like. Conventionally, this frequently takes the form of a system in which a coloured material is released from a reservoir and then immobilised in a detection zone, irrespective of the presence or absence of a specified analyte. Conveniently, the real test system is on one test panel, and the comparator on the other. However, in some embodiments of the present invention, the second test panel is used in an alternative manner, as described below.

As described in the introductory section, when an assay test, such as a home pregnancy test kit, is used without professional supervision, misinterpretation of the test results is surprisingly common. Electronic test units may measure a colour change and accordingly show "Pregnant" or "Not Pregnant" indications on a display screen. However, these units are complex, expensive, use valuable resources and are difficult or impossible to recycle after use, and so are considered ecologically unsound.

Rather than producing a thin line in a detector zone, as for conventional home pregnancy test kits, in embodiments of the present invention, an assay system is used that leads to a significant colour change over a wider area. Thus, as shown in FIG. 2, a two-dimensional coloured area will develop over most or all of one test panel 7, once the assay/test reaction is complete.

As referred to above, the other test panel 8 could still be used for a model reaction, not requiring the presence of the analyte (such as hCG), in order to indicate how a positive result on the first test panel 7 should appear.

Alternatively, however, a different colour-generating system may be used, which only develops a colour change on the second test panel 8, in the absence of the analyte (e.g. hCG). For example, the analyte could bind to antibodies in the coloured material/dye precursor and the substrate in the reservoir, preventing the coloured material/dye precursor from leaving the reservoir and passing to the detection zone. If the analyte is not present, however, the coloured material/dye precursor is entrained in the liquid test sample, passes to the detection zone, and there produces a colour change.

Thus, there would be a first definite colour change on one test panel 7 if the analyte is present, and a second definite colour change on the other test panel 8 if the analyte is not present. This should be easier to read.

Figure 6:
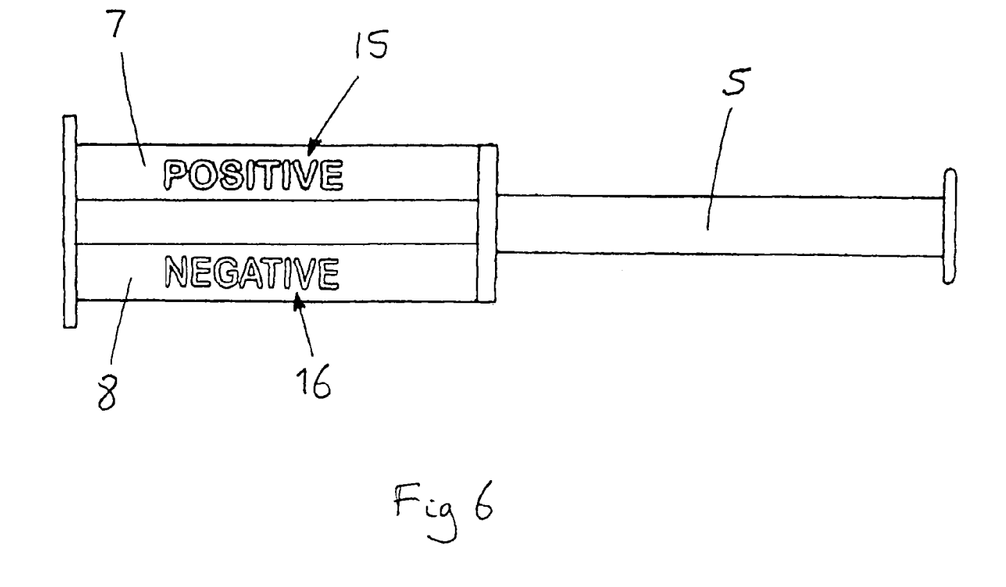
FIG. 6 is a frontal elevation of a test panel assembly of a second assay device embodying the present invention, separated therefrom.
Figure 7:
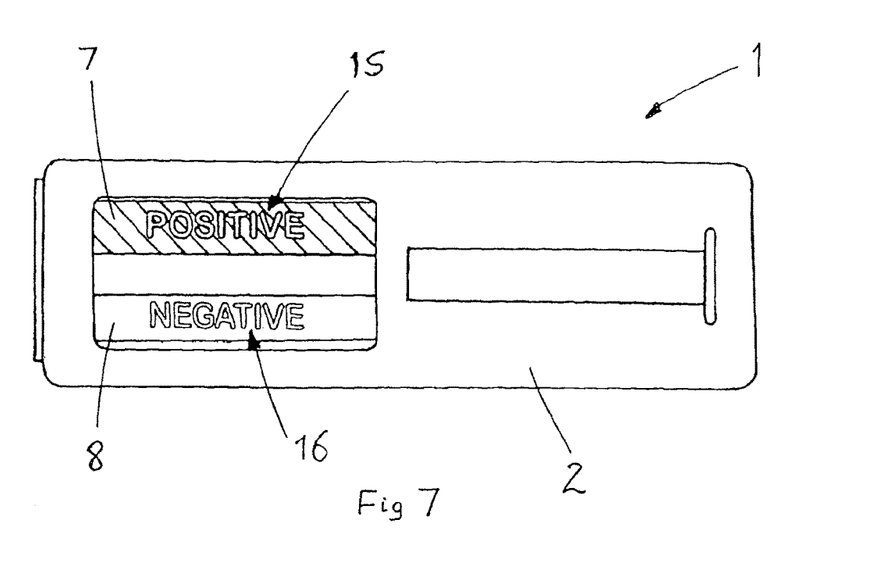
FIG. 7 is a frontal elevation of the assay device of FIG. 6, following a positive test result.

A further development of the present invention, providing even more unmistakeable indications of positive and negative test results, is illustrated by FIGS. 6 and 7. In this embodiment, indicia 15, 16 are formed on one or both test panels 7, 8, which only show up in the event of a positive test result, or only show up in the event of a negative test result, respectively.

As shown in FIG. 6, alternative messages are provided on each test panel 7, 8, using appropriate indicia 15, 16. Symbols or logos could be used (particularly if the device is intended for use in regions of low literacy). However, it is believed that verbal indications are likely to be more unmistakeable. Here, the words "POSITIVE" and "NEGATIVE" are used; for a pregnancy test, "PREGNANT" and "NOT PREGNANT" could be used; the simple terms "YES" and "NO" would be equally viable.

In a first variant of this embodiment, the indicia 15, 16 could be formed on the respective test panels 7, 8 by printing with the appropriate reagent adapted to immobilise an analyte/colour material complex. Alternatively, where a dye precursor/anchored reagent system is being used, the indicia 15, 16 could be printed on to the test panels 7, 8 using the anchored reagent. Thus, in a positive test result, the coloured material collects only where the indicia 15, 16 have been printed with the anchoring reagent (or the dye/pigment is formed only where the indicia 15, 16 have been printed with the appropriate anchored reagent). The relevant indicia 15, 16 will thus appear on a generally un-coloured background of the test panel 7, 8.

However, a second variant of this embodiment is believed to be even easier to read, and may be simpler to produce reliably. In this variant, an ELISA assay test system is used that produces a colour change over most or all of the test panel 7, 8. The indicia 15, 16 could be produced by positioning a mask over each test panel 7, 8 with the indicia 15, 16 printed thereon with white ink; thus, they would be invisible before a reaction has occurred, but once the test panel 7, 8 had changed colour behind the mask, the indicia 15, 16 would become more visible. (A mask with everything except the indicia printed over in white ink could also be used).

However, a more elegant and straightforward approach would be to treat the areas of the test panel 7, 8 corresponding to the indicia 15, 16, such that the colour change of the test panel 7, 8 as a whole either does not occur or does not show up.

Thus, the indicia 15, 16 could be printed with a further active reagent that locally inactivates a colour-forming reaction in the test panel 7, 8, or which locally inactivates an analyte/colour material immobilising reagent (as appropriate to the exact test system in use).

Another approach would be to print the indicia 15, 16 on to the paper (or other porous substrate) of the respective test panel 7, 8 with a clear hydrophobic substance. This would prevent the aqueous test sample even entering the areas of the test panel 7, 8 corresponding to the indicia 15, 16. (The indicia 15, 16 could be printed on to the paper with the hydrophobic substance, before the paper is even impregnated from aqueous solution with the appropriate reagents, combining this concept with that in the previous paragraph).

A third approach would be to print the indicia 15, 16 on to the surfaces of the respective test panel 7, 8 using an opaque white ink. Thus the indicia 15, 16 would again be indistinguishable against the un-coloured background of the test panels 7, 8 before use (or in the event of a negative result). In the event of a positive result, the respective test panel 7, 8 would change colour, revealing the indicia 15, 16 in white against a coloured background.

FIG. 6 thus shows a test panel arrangement in which one test panel 7 is set up to change colour only in the presence of hCG, and has indicia 15 revealed by such a colour change, confirming that this colour change does mean "positive/pregnant". The second test panel 8 is set up to change colour only in the absence of significant levels of hCG, and has indicia 16 to confirm that this colour change does mean "negative/not pregnant".

FIG. 7 thus shows an assay device 1 comprising the test panel arrangement of FIG. 6, after completion of a test indicating pregnancy. The background of the first test panel 7 has changed colour, revealing the indicia POSITIVE 15. The background of the second test panel 8 remains un-coloured, and the indicia NEGATIVE 16 remains invisible.

Figure 8:
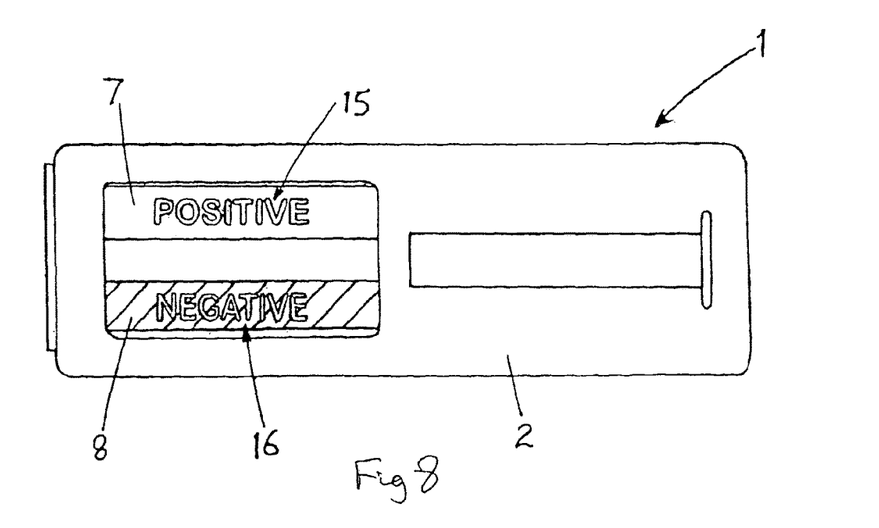
FIG. 8 is a frontal elevation of the assay device of FIG. 6, following a negative test result.

FIG. 8 shows the same assay device 1, after completion of a negative test result. The background of the second test panel 8 has changed colour, revealing the indicia NEGATIVE 16, while the background of the first test panel 7 remains un-coloured, leaving the indicia POSITIVE 15 effectively invisible.

Figure 9:
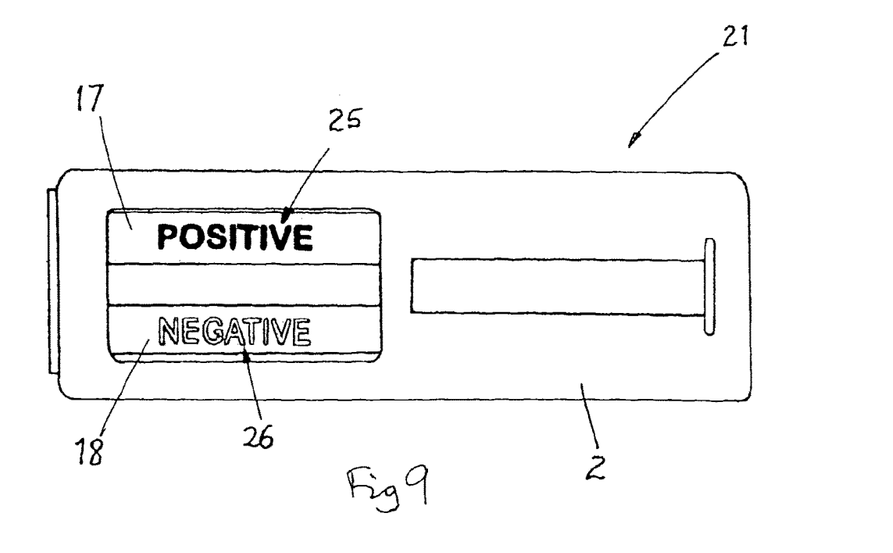
FIG. 9 is a frontal elevation of a third assay device, following a positive test result.
Figure 10:
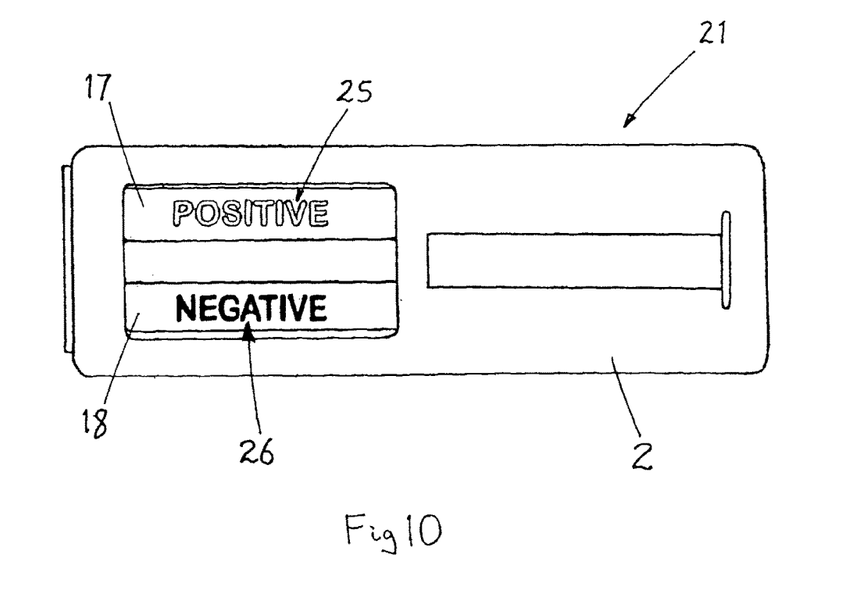
FIG. 10 is a frontal elevation of the assay device of FIG. 9, following a negative test result.

FIGS. 9 and 10 show a third assay device 21 which is identical to that shown in FIGS. 7 and 8, except that it has a first test panel 17 bearing indicia bearing 25 that change colour in the event of a positive test result, and a second test panel 18 bearing indicia 26 that change colour in the event of a negative test result. The backgrounds of these test panels 17, 18 do not change colour.

Thus, FIG. 9 shows the third assay device 21 after a test has been carried out with a positive result. The indicia POSITIVE 25 have changed colour against an unchanged background of the first test panel 17, while the indicia NEGATIVE 26 have not changed colour, and are not visible against the unchanged background of the second test panel 18. Conversely, FIG. 9 shows the device 21 after a test with a negative result. The indicia NEGATIVE 26 have changed colour and are visible against an unchanged background of the second test panel 18, while the indicia POSITIVE 25 have not changed colour and are not visible against the unchanged background of the first test panel 17.

N.B: In FIGS. 6 to 10, the outlines of the indicia 15, 16, 25, 26 are shown for clarity, even where the indicia 15, 16, 25, 26 would be the same colour as the background and effectively invisible in practice.

Another embodiment of the present invention employs an alternative approach to immobilising the coloured material in the detection zone. It is known to produce latex particles containing magnetic particulate material, or to produce magnetic particulate material treated to be dispersible in an aqueous system. The ferro-magnetic microparticles used in the coatings on recording tapes and discs are a convenient example. If the antibody/analyte reaction is used to release these materials from the reservoir, then simple magnetic attraction may be used to immobilise them once they reach the detection zone. Thus, a magnetic/ferrous plate located beneath the substrate in the detection zone could lead to the magnetic particles being immobilised over a two-dimensional area. Alternatively, a linear magnetic/ferrous feature extending beneath the substrate could produce a classic line to indicate a positive result. Additionally, indicia forming verbal messages (similar to those shown in FIGS. 6 and 7) could be generated by locating appropriately-shaped magnetic/ferrous features beneath the substrate in the detection zone.

Such magnetic particulate material usually has an intense colour, in the dark brown to black range, and so may act as its own coloured material to produce visual changes in the detection zone. However, other coloured materials may be bonded to the magnetic material if required (for example, both could be incorporated into the same latex particles, or the coloured material and the magnetic material might be flocculated or coacervated into composite particles).

As briefly mentioned above, a major aim of the present invention is to provide a device that may be disposed of after use without significant environmental damage. Thus it is preferred if the components of the assay device 1 are all environmentally degradable. The paper of the test panels 7, 8 is likely to be easily degradable to environmentally neutral fibres, but a remainder of the assay device 1 also needs to be made from a material that is durable on storage, and sufficiently strong for a user not to have to worry about breaking the assay device 1 (which will often be used by persons under significant stress).

Most plastics materials would be suitable, apart from their resistance to environmental degradation. Some polymers have been developed that are biodegradable under particular conditions, including PHB (polyhydroxybutyrate), PLA (polylactic acid) and PCLs (polycaprolactones). However, these materials are currently far more expensive than simple polyolefins such as polyethylene or polypropylene. They can be composted anaerobically, but they are much less ready to decompose in aerobic conditions, such as if disposed of to landfill. In many cases, particularly in developing countries, polymer items are simply dumped, rather than being taken to a special disposal facility. Thus, aerobic degradation would be the only available route. In any case, anaerobic processes may lead to the production of methane, which is a particularly undesirable "greenhouse gas". Additionally, they are not easy to recycle and would need to be kept separate from other recycled polymer streams, to avoid ruining the properties of the recycled polymer. Some of these polymers might even react with the reagents used in the device.

The approach that is considered most useful in the present invention is variously known as "bioassimiliation" or "oxo-biodegradation". A major problem with biodegradation of polyolefins, such as polyethylene and polypropylene, is the sheer length of the hydrocarbon chains that make up the polymer and which offer no easy point of attack for micro-organisms. However, if the hydrocarbon chains were shorter, the polyolefin would lose its physical strength and rigidity. Polyolefins thus bio-degrade very slowly, over years or decades.

It is now believed that the surface of a polyolefin will very gradually oxidise in air, this oxidative cleavage of the hydrocarbon chains shortening them and leaving polar end groups, both encouraging subsequent microbiological attack and consumption of the chain fragments. This oxidation may also be photo catalysed by UV light. However, relying on surface oxidation to degrade a polyolefin object is far too slow.

Recently, additives for polyolefins (known as "pro-degradants") have been developed that significantly increase oxidative attack on the hydrocarbon chains. The pro-degradant catalyses the initial aerial oxidation of the polyolefin's hydrocarbon chains, and because it is blended throughout the bulk of the polyolefin, this effect should not be limited to the surface of the polyolefin alone. Additionally, once chain cleavage is under way, the polyolefin becomes brittle, and will physically break down into flakes or other smaller bodies, increasing the surface area for catalysed aerial oxidation. A typical polyethylene hydrocarbon chain may have a molecular mass of around 300,000 units, but the pro-degradant, in aerobic conditions, can rapidly bring the average molecular mass down to below 40,000 units.

At this molecular mass, the chain fragments are sufficiently small for microbiological attack. Additionally, the polar end-groups generated by the oxidation have by that stage reached a sufficient concentration that the polyolefin becomes water-wettable, and micro-organisms can readily grow across the polyolefin surface and start to "eat" the chain fragments.

From this stage onwards, the process is a true biodegradation process, as it is wholly mediated by micro-organisms, which will "chew" along the chain fragments, converting carbon and hydrogen to water and biomass, and eventually to carbon dioxide plus water. This is a far less harmful final product than methane from anaerobic digestion. The entire process is thus aptly termed oxo-biodegradation.

The pro-degradant may be incorporated into the polyolefin during processing, conveniently in the form of a concentrate or "master-batch" containing high levels of pro-degradant dispersed in the appropriate polyolefin.

A range of such pro-degradants is currently available. For example, the British company Symphony Plastics Ltd currently offers a pro-degradant additive under the registered trade mark "d$_2$w". The US company Willow Ridge Plastics, Inc offers pro-degradants under the brands PDQ, PDQ-H and BDA. EPI Environmental Products Inc of Canada offers a pro-degradant under the brand name TDPA. Wells Plastics Limited, of the UK, offers master-batch products containing pro-degradant additives under the brand name "Reverte".

It is believed that the common component in these additives is the presence of metal salts, and in particular transition metal salts. Salts of organic compounds are believed to be most effective, possibly due to their ease of incorporation. Long-chain carboxylates, such as stearates or oleates, or aromatic salts such as naphthenates, appear particularly suitable. Cobalt, iron, zinc, manganese, cerium and nickel carboxylate salts have all been cited as effective pro-degradant components, but most transition metals and many non-transition metals have been proposed as being suitably active in the form of a salt of a carboxylate or other such organic compound.

It is suggested that a readily-available source of mixtures of such active metal salts is the residue from petroleum distilling. In any case, the presence of petroleum derived hydrocarbons having moderately high chain length (though much lower than the chain lengths of polyolefins) is suggested in itself to aid the oxo-biodegradation process.

These pro-degradants have been used in thin film LDPE, such as in carrier bags. There appears to be a direct relationship between the level of prodegradant (1-3% by weight of the pro-degradant concentrate in LDPE film is typical) and the speed of the onset of biodegradation. It is thus possible to select a desired lifetime for the LDPE film (in broad terms). This relationship also allows polyolefins containing the pro-degradant to be blended (at low proportions) into ordinary PE recycling streams, since the pro-degradant will be evenly dispersed throughout the recycled PE, at a level not significantly affecting its durability.

Figure 11:
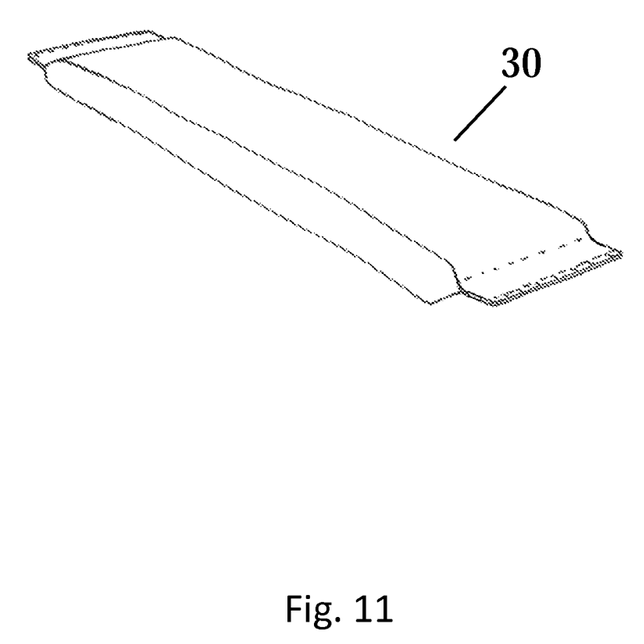
FIG. 11 illustrates a sealed pouch enclosing an immunoassay testing device.

Such additives appear not to have been used previously in bulk polyethylene and polypropylene mouldings, such as would be required for most components of the assay devices of the present invention. In the present invention, a level of pro-degradant can be selected and incorporated into the polyolefin prior to moulding, to give a reasonable oxo-biodegradation rate once the device has been used and disposed of in landfill, or by other aerobic disposal methods, while allowing recycling as "pure" polyolefin, if preferred. If there is a concern about oxidation taking place prior to use, premature oxidation should be obviated by storage in sealed, UV-opaque pouches 30, as illustrated in FIG. 11, preferably either vacuum-sealed or filled with an inert atmosphere.

The pro-degradant additives appear to have little effect on the physical properties of a polymer into which they are incorporated, and some have been approved for food contact by the FDA, so there are unlikely to be significant hazards associated with their use. Additionally, the cost per tonne of the pro-degradant is little more than that of the polyolefin, while specialist bio-degradable plastics can be ten or twenty times more expensive.

Measured in terms of the pure metal salts, the pro-degradant may be sufficiently effective at levels as low as 0.05% by weight. However, for a significant effect on biodegradability, it is likely that levels of up to 0.1%, 0.5% or even 1% may be needed, depending on the speed of breakdown required. Considered as a master-batch level, the blending of 1-3% by weight of the concentrate appears to be a good starting point. Low levels would retard the biodegradation, but raise shelf life. Higher levels should give more rapid degradation after disposal, but may possibly harm other properties, such as colour and physical properties, if levels were raised too far.

The precise level for each use should thus be straightforward to optimise. There is now an American Society of Testing & Materials (ASTM) standard for testing oxo-biodegradable materials (ASTM D6954-04), and a British Standard is currently in draft (BS8472). It should therefore be relatively routine to assess the performance of different additive levels for a desired outcome.

Other conventionally-used additives may be used in the polymer, such as additives to keep the polymer stable at high temperatures during processing, and photostabilisers to prevent premature degradation under ultraviolet irradiation. Alternatively, normal photostabiliser levels may be reduced, so that UV-initiated degradation may reinforce the effect of the oxo-biodegradation.

Therefore, it is believed that rendering the casing 2 and other components of the assay device 1 oxo-biodegradable, for example by adding a pro-degradant, should obviate existing problems with the disposal into landfill of tens or hundreds of millions of assay devices, while not harming any other important properties.

One possible problem with the oxo-biodegradation processes described above is that they can be slowed significantly in cold conditions. Thus, for products intended for use in Canada, Scandinavia and Russia, for example, ambient conditions for much of the year would result in decelerated degradation of disposed polymer.

In such cases, an alternative approach may be preferred. It is known to fill polyolefins, particularly LDPE, with micro-particles of solid starch, typically at levels of up to 15% by weight. The starch granules (or other biopolymers) are immediately accessible to microbiological attack, causing the polyolefin (relatively) rapidly to disintegrate into fragments having relatively low ecological impact. Starch-filled polymers cannot be recycled in ordinary recycling streams, and at high levels, polymer strength may be impaired. Thus, in many cases, oxo-biodegradable systems would probably be preferred. However, where the oxo-biodegradation process is potentially slowed, starch-filled polymers should comprise a suitable alternative.

The starch granules and the pro-degradant additives should be mutually compatible, and so it should be possible to incorporate both into a single polymer if desired.

The invention claimed is:

1. An immunoassay testing device for detecting an analyte comprising an immunoassay testing element mounted to a structure, said structure comprising a casing adapted to enclose the immunoassay testing element, wherein the casing comprises a plastics material durable on storage but adapted to be environmentally degradable, said plastics material comprises an oxo-biodegradable plastics material, degradation of the material being initiated by reaction with oxygen, and said immunoassay testing element comprises a first test panel and a second test panel, the first test panal including first means for detecting and indicating, by a first color change, presence of the analyte, and the second test panel including second means for detecting absence of said analyte and indicating said absence by a second color change, wherein said second means develops said second color solely in response to the absence of the analyte and not in the presence of the analyte, whereby said immunoassay testing device unambiguously indicates analyte presence by the first color change or analyte absence by the second color change.

2. The immunoassay testing device as claimed in claim 1, wherein substantially all of the structure of the device comprises said environmentally degradable plastics material.

3. The immunoassay testing device as claimed in claim 1, wherein the oxo-biodegradable plastics material is adapted to complete its environmental degradation under microbiological action.

4. The immunoassay testing device as claimed in claim 1, wherein the environmentally degradable plastics material comprises a plastics material filled with particles of a more readily biodegradable material.

5. The immunoassay testing device as claimed in claim 1, wherein the environmentally degradable plastics material comprises a plastics material blended with an additive adapted to promote oxidative degradation of the plastics material.

6. The immunoassay testing device as claimed in claim 5, wherein said additive to promote oxidative degradation comprises at least one metal salt.

7. The immunoassay testing device as claimed in claim 5, wherein said additive to promote oxidative degradation comprises a long-chain hydrocarbon-based material.

8. The immunoassay testing device as claimed in claim 5, wherein said additive to promote oxidative degradation comprises at least one metal carboxylate.

9. The immunoassay testing device as claimed in claim 5, wherein said additive to promote oxidative degradation comprises a long-chain hydrocarbon-based material derived from petroleum refining residues.

10. The immunoassay testing device as claimed in claim 1, comprising a pregnancy test device.

11. The immunoassay testing device as claimed in claim 1, wherein the immunoassay testing devices is wholly disposable.

12. The immunoassay test device as claimed in claim 1, wherein said first color change extends throughout a two-dimensional area of test material.

13. The immunoassay test device as claimed in claim 12, wherein said two-dimensional area comprises indicia.

14. The immunoassay test device as claimed in claim 1, wherein said second color change extends throughout a two-dimensional area of test material.

15. The immunoassay test device as claimed in claim 14, wherein said two-dimensional area comprises indicia.

16. An immunoassay testing device for detecting an analyte comprising an immunoassay testing element mounted to a structure, said structure comprising a casing adapted to enclose the immunoassay testing element, wherein the casing comprises a plastics material durable on storage but adapted to be environmentally degradable, said plastics material comprises an oxo-biodegradable plastics material, degradation of the material being initiated by reaction with oxygen, and said immunoassay testing element comprises a first test panel and a second test panel, the first test panel including first means for detecting and indicating, by a first color change, presence of the analyte, and the second test panel, independent from the first test panel, including second means for detecting absence of said analyte and indicating said absence by a second color change, wherein said second means develops said second color solely in response to the absence of the analyte and not in the presence of the analyte, whereby the said immunoassay testing device unambiguously indicates analyte presence by the first color change or analyte absence by the second color change.

17. The immunoassay testing device as claimed in claim 16, wherein the second test panel is separate from the first test panel.

18. An immunoassay testing device for detecting an analyte comprising an immunoassay testing element mounted to a structure, said structure comprising a casing adapted to enclose the immunoassay testing element, wherein the casing comprises a plastics material durable on storage but adapted to be environmentally degradable, said plastics material comprises an oxo-biodegradable plastics material, degradation of the material being initiated by reaction with oxygen, and said immunoassay testing element comprises a first test panel and a second test panel, operable in tandem, the first test panel including first means for detecting and indicating, by a first color change, presence of the analyte, and the second test panel including second means for detecting absence of said analyte and indicating said absence by a second color change, wherein said second means develops said second color solely in response to the absence of the analyte and not in the presence of the analyte, whereby said immunoassay testing device unambiguously indicates analyte presence by the first color change or analyte absence by the second color change.

19. The immunoassay testing device as claimed in claim 18, wherein the second test panel is separate from the first test panel.

* * * * *

UNITED STATES PATENT AND TRADEMARK OFFICE
CERTIFICATE OF CORRECTION

PATENT NO. : 10,234,452 B2
APPLICATION NO. : 13/390154
DATED : March 19, 2019
INVENTOR(S) : Jennifer Mary Benson It is certified that error appears in the above-identified patent and that said Letters Patent is hereby corrected as shown below:

In the Claims

Column 13, Line 31: Claim 1, Delete "panal" and insert -- panel --

Signed and Sealed this
Seventh Day of May, 2019

Andrei Iancu
*Director of the United States Patent and Trademark Office*